US010857318B2

(12) United States Patent
Enk et al.

(10) Patent No.: US 10,857,318 B2
(45) Date of Patent: Dec. 8, 2020

(54) GAS FLOW REVERSING ELEMENT WITH BYPASS AND METHOD FOR CONTROLLING EXPIRATION OF A PATIENT

(71) Applicant: VENTINOVA TECHNOLOGIES B.V., Eindhoven (NL)

(72) Inventors: Dietmar Enk, Coesfeld (DE); Dirk Theodorus Andreas Van Asseldonk, Veghel (NL)

(73) Assignee: Ventinova Technologies B.V., Eindhoven (NL)

( * ) Notice: Subject to any disclaimer, the term of this patent is extended or adjusted under 35 U.S.C. 154(b) by 1038 days.

(21) Appl. No.: 14/904,002

(22) PCT Filed: Jul. 10, 2014

(86) PCT No.: PCT/EP2014/064801
§ 371 (c)(1),
(2) Date: Jan. 8, 2016

(87) PCT Pub. No.: WO2015/004229
PCT Pub. Date: Jan. 15, 2015

(65) Prior Publication Data
US 2016/0166789 A1 Jun. 16, 2016

Related U.S. Application Data

(60) Provisional application No. 61/844,746, filed on Jul. 10, 2013.

(51) Int. Cl.
*A61M 16/00* (2006.01)
*A61M 16/04* (2006.01)
(Continued)

(52) U.S. Cl.
CPC .... *A61M 16/0009* (2014.02); *A61M 16/0012* (2014.02); *A61M 16/0057* (2013.01);
(Continued)

(58) Field of Classification Search
CPC .............. A61M 16/00; A61M 16/0009; A61M 16/0012; A61M 16/0833; A61M 16/201;
(Continued)

(56) References Cited

U.S. PATENT DOCUMENTS 3,581,742 A   6/1971   Glenn
3,859,995 A   1/1975   Colston
(Continued)

FOREIGN PATENT DOCUMENTS

GB   714773   9/1954
GB   806471   12/1958

OTHER PUBLICATIONS

European Patent Office. International Application No. PCT/EP2014/064801. International Search Report dated Oct. 15, 2014. English Language. 5 pages.
(Continued)

*Primary Examiner* — Samchuan C Yao
*Assistant Examiner* — Ned T Heffner
(74) *Attorney, Agent, or Firm* — Occhiuti & Rohlicek LLP (57) ABSTRACT

Gas flow reversing element (1) for the use of a gas supply (14) under excess pressure, in particular inspiratory gases, for selectively generating a gas flow (8) from or to a line connector (6) which can in particular be connected to an airway of a patient, said gas flow reversing element (1) being designed as a main piece (2), the main piece (2) at least comprising an inflow region (9), a nozzle region (15) and a mixing region (16), and further a branching piece (3), the
(Continued)

inflow region (9) connecting a pressure connector (4), for connection to the gas supply (14), to at least one closable outlet opening (5) arranged in the mixing region (16), and the branching piece (3) connecting the nozzle region (15) of the main piece (2) to the line connector (6), wherein a nozzle (7), particularly an injector nozzle, is configured and arranged in the nozzle region (15) in such a way that, a gas flow (8) flowing along a first flow path (20) through the main piece (2) from the pressure connector (4) subsequently through the inflow region (9), the flow region (28), the nozzle region (15) and through the nozzle (7) into the mixing region (16) to the outlet opening (5), with the outlet opening (5) opened, can generate a gas flow (8) in the branching piece (3) flowing along a second flow path (21) from the line connector (6) and subsequently through the branching piece (3), through the nozzle region (15) and through the mixing region (16) to the outlet opening (5), wherein the gas flow reversing element (1) further comprises a bypass (18) connecting the pressure connector (4) and the line connector (6) so that a gas flow (8) can flow along a third flow path (22) via the inflow region (9), the bypass (18) and the branching piece (3), wherein at least the bypass (18) and the flow region (28) are closable by at least one closing element (19), so that the gas flow (8) can bypass the nozzle (7) in the nozzle region (15) via the bypass (18) along the third flow path (22). The invention further relates to method for controlling expiration of a patient.

9 Claims, 4 Drawing Sheets (51) Int. Cl.
*A61M 16/12* (2006.01)
*A61M 16/20* (2006.01)
*A61M 16/08* (2006.01)
*A61M 16/16* (2006.01)
*A61M 16/14* (2006.01)
*A61M 16/10* (2006.01)

(52) U.S. Cl.
CPC ...... *A61M 16/0096* (2013.01); *A61M 16/022* (2017.08); *A61M 16/0434* (2013.01); *A61M 16/0816* (2013.01); *A61M 16/0833* (2014.02); *A61M 16/12* (2013.01); *A61M 16/201* (2014.02); *A61M 16/0063* (2014.02); *A61M 16/085* (2014.02); *A61M 16/1075* (2013.01); *A61M 16/14* (2013.01); *A61M 16/16* (2013.01); *A61M 2016/0027* (2013.01); *A61M 2202/0208* (2013.01); *A61M 2230/432* (2013.01)

(58) Field of Classification Search
CPC ............ A61M 16/022; A61M 16/0057; A61M 16/0096; A61M 16/0434; A61M 16/0816; A61M 16/12; A61M 16/0063; A61M 16/085; A61M 16/1075; A61M 16/14; A61M 16/20–209; A61M 16/06–0694; A61M 16/0003–0012; A61M 2016/0027; A61M 16/0015–0042; A61M 2201/02; A61M 2230/432
See application file for complete search history.

(56) References Cited

U.S. PATENT DOCUMENTS

| 4,595,004 | A | * | 6/1986 | Czech | ............... | A61M 16/0096 |
| | | | | | | 128/200.21 |
| 5,388,571 | A | * | 2/1995 | Roberts | ................. | A61M 16/16 |
| | | | | | | 128/200.18 |
| 6,443,154 | B1 | * | 9/2002 | Jalde | ..................... | A61M 16/20 |
| | | | | | | 128/201.28 |
| 2010/0236551 | A1 | * | 9/2010 | Enk | ....................... | A61M 16/00 |
| | | | | | | 128/204.18 |

OTHER PUBLICATIONS

"International Preliminary Report on Patentability issued for PCT/EP2014/064801 dated Jan. 12, 2016".

* cited by examiner

GAS FLOW REVERSING ELEMENT WITH BYPASS AND METHOD FOR CONTROLLING EXPIRATION OF A PATIENT

The present invention relates to a gas flow reversing element and to a method for operating it, so that selectively a gas flow from or to a line connector for gas exchange in sealed or partially sealed (partial) areas of the airway of a patient is generated. The present invention relates further to a method for ventilation of a patient via a gas flow reversing element. The present invention relates further to a method controlling expiration of a patient. One use involves connecting such a gas flow reversing element to a lumen, such as a catheter or a needle, or to a multitude of sequentially connected and/or parallel lumen (bronchusscope, bronchusblocker, larynchoscope, etc.) being insertable into the airways of a patient.

To ventilate a patient, a mask or a tube is normally used by way of which a gas or gas mixture, in particular oxygen and air, is delivered at low pressure to the airway sealed off from the outside. Alternatively, however, a gas or gas mixture of this kind can also be injected in pulses at a high pressure and a high flow rate through a thin, unblocked catheter into the airway lying open to the outside (jet ventilation). This method is nowadays used particularly in diagnostic and therapeutic interventions in the area of the upper airway or of the lung. By means of this method, however, a patient can also be supplied with oxygen via a catheter introduced through the skin directly into the trachea or via a needle positioned in this way (transtracheal jet ventilation). This special method is one of the currently available options for management of a difficult airway and, in particular, for management of the situation in which a patient cannot be conventionally ventilated or intubated (a "cannot ventilate, cannot intubate" situation).

Under unfavorable conditions, however, jet ventilation can also be potentially lifethreatening. If a patient's airway is substantially or even completely obstructed, for example by swelling or bleeding, the patient's lung becomes more and more distended by injection of oxygen. There is then a risk of barotrauma. The increase in pressure in the thorax can also lead to a circulatory disturbance, which is of no less danger to the patient, or to a circulatory collapse, since the blood is unable to flow back in sufficient quantity to the heart.

US 2010-0236551 A1 describes a gas flow reversing element with which a patient can be normoventilated, that is the patient can be provided with sufficient inspiratory gases and at the same time expiratory gases can be removed from the patient via the gas flow reversing element so that no further ventilation actions have to be applied. The patient can therefore be ventilated only via the gas flow reversing element for a virtually unlimited period of time. Nevertheless, in cases in that patients are ventilated for a prolonged period of time moisturizing of the inspiratory gases is necessary. Further, liquids or other gases are mixed to the inspiratory gas for providing medication or anesthesia to the patient. Due to the nozzle provided in the gas flow reversing element a pressure drop is induced to the gas flow. This pressure drop at the nozzle can cause condensation of the gases or liquids of the inspiratory gas flow. Thereby, it is possible that the gas flow reversing element is obstructed by liquids stemming from condensation of the inspiratory gas flow. Further, it can not be ensured that the intended amount and concentration of medication and/or anesthesia is provided to the patient.

Accordingly, the object of the present invention is to make available a simple device and a method by which inspiratory gases can be delivered to the lung, but by which carbon dioxide or used air can also be actively withdrawn from the lung in sufficient quantity, wherein at the same time it is ensured that this ventilation of the patient is possible for a virtually unlimited period of time. Further a method of controlling expiration of a patient is proposed which diminishes the problem of injuries to the lung induced by shear stresses during expiration. In addition, controlling expiration by suction enables negative pressure ventilation which can be of particular importance to stimulate venous return and by that promote resuscitation.

This object is achieved by a gas flow reversing element with features as claimed herein. Advantageous developments and configurations of the gas flow reversing element and of the methods are the subject matter of the respective dependent claims. The features specified individually in the claims and in the description (and related to device or method only) may be combined with one another in any desired technologically meaningful way and may be supplemented by explanatory facts from the description, with further embodiments of the invention being specified.

The gas flow reversing element according to the invention serves for the use of a gas supply under excess pressure, in particular inspiratory gases, for selectively generating a gas flow from or to a line connector which can in particular be connected to or inserted into an airway of a patient. The gas flow reversing element is being designed as a main piece, with the main piece at least comprising an inflow region, a flow region, a nozzle region and a mixing region, and further a branching piece. The inflow region connects a pressure connector, for connection to the gas supply, to at least one closable outlet opening arranged in the mixing region. The branching piece connects the nozzle region of the main piece to the line connector, wherein a nozzle, particularly an injector nozzle, is configured and arranged in the nozzle region in such a way that, a gas flow flowing along a first flow path through the main piece from the pressure connector subsequently through the inflow region, the flow region, the nozzle region and through the nozzle into the mixing region to the outlet opening, with the outlet opening opened, can generate a gas flow in the branching piece flowing along a second flow path from the line connector and subsequently through the branching piece, through the nozzle region and through the mixing region to the outlet opening. The gas flow reversing element further comprises a bypass connecting the pressure connector and the line connector so that a gas flow can flow along a third flow path via the inflow region, the bypass and the branching piece. At least the bypass and the flow region are closable by at least one closing element, so that the gas flow can bypass the nozzle in the nozzle region via the bypass along the third flow path.

The gas flow reversing element according to the invention corresponds in particular to the gas flow reversing element disclosed in US 2010-0236551 A1, wherein according to the present invention a bypass and closing elements are proposed. It is for that reason that US 2010-0236551 A1 and its complete disclosure is referenced herewith.

According to a preferred embodiment of the gas flow reversing element with bypass the at least one closing element is a 3/2-way valve. A 3/2-way valve is a valve which can be switched between two positions to connect three ducts differently with each other. In this case the pressure connector can be either connected to the flow region or to the bypass. At the same time the not-connected duct (the bypass or the flow region) is closed off by the valve.

According to another preferred embodiment of the gas flow reversing element two scissor-valves are provided as the at least one closing element. Preferably, one (first) scissor-valve is being positioned at the third flow path, for example in the area of the bypass. The other (second) scissor-valve is being positioned at the first flow path, for example between the inflow region and the flow region. Being positioned between the inflow region and the flow region, the (second) scissor-valve can control the flow of inspiratory gas along the first or fourth flow path. Further it can control the expiratory gas flow along the second flow path. The other (first) scissor-valve can be positioned at the bypass and therefore controls the inspiratory gas flow along the third flow path.

The term "scissor valve" refers to valves that close a flexible tube by squeezing it from the outside (these are known from the art). Therefore, the valves are not in direct contact with the inspiratory or expiratory gases and can therefore not become polluted. Scissor valves do not necessarily switch between "open" and "closed" states. Preferably, a gradual opening and closing is possible. Further, the scissor valves can be operated synchronously. For example, one can be opened while the other is being closed or vice versa. Preferably, the scissor valves are controlled independently so that individual control of each scissor valve is possible.

According to a preferred embodiment also the outlet opening is provided with a scissor-valve as closing element.

According to another preferred embodiment the outlet opening or the mixing region can be opened/closed/manipulated by a scissor valve. Preferably, the gas flow through the outlet opening is manipulated (opened/closed) by a scissor valve which is positioned along the mixing region.

In particular, the closing elements are pinch valves instead of scissor valves. A pinch valve is a full bore or fully ported type of control valve which uses a pinching effect to obstruct fluid flow.

Preferably, all closing elements may be operated either independently or if needed, synchronously. Preferably, all closing elements allow for gradual opening and closing so that volumetric flow rate along each flow path is controllable and to be regulated by the closing elements.

In particular, for an excess pressure of 1 to 8 bar above atmospheric pressure at the pressure connector and with the outlet opening being closed, the third flow path, connecting the pressure connector and the line connector via the bypass, has a first pressure loss deltaP1. Further, a fourth flow path, connecting the pressure connector and the line connector via the inflow region, the flow region, the nozzle region, and the branching piece, has a second pressure loss deltaP2. For the gas flow reversing element the following relation between deltaP1 and deltaP2 is fulfilled (with respective closing elements fully opened or fully closed):

$$deltaP2 > 2*deltaP1.$$

In particular, the pressure loss deltaP1 of the third flow path is much smaller than the pressure loss deltaP2 along the fourth flow path. Therefore, especially at intended flow rates of 12 l/min [liters per minute] or more, for which the pressure loss deltaP2 along the fourth flow path is high (approximately more than 1.8 bar), inspiratory gas can be provided via the third flow path instead.

It has been established that for flow rates of around 15 l/min the pressure loss deltaP2 is around 2 bar. For flow rates of 25 l/min pressure loss deltaP2 can be as high as 3.5 bar. This is especially problematic in surroundings in which compressed gas sources can only deliver around 3 bar (as for example in hospitals in the USA, in which around 50 psi [pounds per square inch] are usually provided; 50 psi corresponds to 3.45 bar). Furthermore, the pressure loss is further increased by flow control means which may be positioned upstream of the gas flow reversing element. This problem is further aggravated at certain points of time at a day (for example in the morning), when all operation rooms in a hospital are started up in parallel. In this case the available pressure from the compressed gas sources can be much smaller than usual.

According to a further preferred embodiment, the mixing channel and the nozzle are configured and arranged in the main piece in such a way that, by a gas flow flowing along the first flow path with the outlet opening opened, the gas flow flowing along the second flow path can also be generated, specifically with a volumetric flow rate which, at an excess pressure of 0.5 to 8 bar above atmospheric pressure at the pressure connector, is at least 1 l/min [liters per minute], preferably at least 2 l/min or even at least 3 l/min.

Preferably, the volumetric flow rate of at least 3 l/min along the second flow path is already possible with an excess pressure of 0.5 to 1.5 bar above atmospheric pressure at the pressure connector. In particular, the volumetric flow rate of at least 8 l/min along the second flow path is already possible with an excess pressure of 1 to 5 bar above atmospheric pressure at the pressure connector.

The bypass allows now for a third flow path through the gas flow reversing element. The bypass allows the inspiratory gas, supplied via the pressure connector, to bypass the nozzle region. In that way the pressure drop, induced by the nozzle inside the nozzle region, does not affect the volumetric gas flow flowing along the third flow path into a patient's airways. Therefore, the inspiratory gas can be provided to the patient's airway directly via the bypass with a not further limited gas flow rate and without further (relevant) pressure drop. Furthermore, possible condensation of any contents of the inspiratory gas inside the gas flow reversing element is (almost completely or even completely) prevented. It is for that reason that inspiratory gas can be provided to the patient as high pressure gas flow (pressure is not reduced by nozzle because it is provided via the bypass) with a higher flow rate.

It is possible to provide moistened and possibly also heated inspiratory gases to the patient via the gas flow reversing element. The term "inspiratory gas" refers in general to at least one of the following:

medical oxygen, air, mixture of oxygen and air; these gases with additional moistening (water damp); these gases with additional anesthesia "gases" (often called "damp" as well because anesthesia is often applied to inspiratory gas as a liquid); all possible other kinds of gases and (droplets) of liquid/damp to be added to the patient. Therefore, inspiratory gases are not only gases, but also include two-phase systems such as liquids being dissolved or dispersed in a gas phase.

The provision of moistened and possibly heated inspiratory gases to a patient's airway is regarded crucial for longer term mechanical ventilation, as is generally known. Longer term mechanical ventilation is often necessary in complicated or large surgical procedures and for patients on the intensive care units (ICU).

The bypass can now be used for delivering (heated and) moistened inspiratory gas to the patient. In particular the inspiratory gas is provided as high pressure gas flow into the patient's airway via the bypass along the third flow path. This is a major improvement over the gas flow reversing element as is disclosed in US 2010-0236551 A1. There, the nozzle makes it difficult to administer water damp and/or anesthesia damp (or damp of other active compounds/drugs (="medicine")) as intended because the high pressure drop in the nozzle induces condensation. The inspiratory gas can therefore be provided along the third flow path with closely monitored pressure, wherein at the same time it is ensured that the provided medication/anesthesia is being forwarded into the airway's of the patient without loss or delay. The bypass is especially advantageous for applications in which the gas flow entering the gas flow reversing element via the pressure connector is already provided with moisture or medicine.

In particular, the high pressure gas flow (flowing along the third flow path along the bypass) is used for weaning procedure of the patient.

Weaning means here the procedure of withdrawing mechanical ventilation wherein autonomous breathing of the patient is ensured at the same time. It refers to the problem that patients have to be closely monitored after withdrawal of mechanical ventilation because the patients have to regain control of autonomous breathing. The process of weaning is generally known in the art.

The gas flow reversing element is especially designed to support the weaning procedure. Prior to withdrawal of the lumen, being connected to the line connector and inserted into the airway of a patient and used for ventilation of the patient, from the patient's airways, a high pressure gas flow is provided to the patient along the third flow path via the bypass. In that way the nozzle region of the gas flow reversing element is bypassed, so that the pressure drop at the nozzle is not reducing the pressure of the gas flow intended to be provided to the patient.

It is further proposed that a lumen (being connected to the line connector and inserted into the patient's airway) is provided with a cuff so that the airway of the patient around the lumen is at least partially (preferably completely) obstructed by the inflated cuff. In that case the ventilation of the patient with inspiratory gas is conducted via the gas flow reversing element, wherein the cuff is deflated at the time when the high pressure gas flow is provided to the patient via the bypass along the third flow path. In that case, extensive volume of inspiratory gas can bypass the cuff and exit to the outside of the patient's airway.

In particular, a lumen is provided with a cuff so that the airway of the patient around the lumen is at least partially (preferably completely) obstructed by the inflated cuff. The ventilation of the patient is conducted via the gas flow reversing element, wherein the cuff is inflated at the time when the high pressure gas flow is provided to the patient via the bypass along the third flow path. This is especially advantageous in cases in which a certain volumetric inspiratory gas flow needs to be applied but when there is not enough pressure available to obtain this flow via the fourth flow path (via the nozzle region). The required higher volumetric gas flow of inspiratory gases can then be directed via the third flow path. The lower pressure available at the pressure connector is used for inducing the expiratory gas flow via the second flow path with a reduced expiratory gas flow rate. In particular, this applies for cases of ventilations in which a ratio of inspiration time/expiration time of approximately 1:2 are intended. That means that for example inspiration is conducted for two seconds at 20 l/min [liters per minutes] and expiration for 4 seconds at 10 l/min. The decreased flow rate during expiration is sometimes intended because the pressure needed for support of expiration can in that case be decreased.

It may be necessary to add medicaments to the gas or gas mixture. For this purpose, a closable side access can be arranged, in particular in the area of the branching piece, preferably between the connection of bypass and branching piece and the line connector. Thus, for example, adrenaline, local anesthetics, expectorants and the like (in the following referred to as "medicine") can be conveyed in finely atomized form to the patient by means of the rapidly flowing inspiratory gas or gas mixture. In this way, a medicament can be distributed effectively and over a large surface area into the airway and is thus more rapidly absorbed by the patient. In addition or alternatively, water damp or water in liquid form can be provided to the gas flow for damping the inspiratory gas flow flowing through the branching piece.

Alternatively, the side access can be provided downstream (considering the third or fourth flow path) of the branching piece or even downstream of the line connector. Preferably the side access is provided directly to the lumen being connected to the line connector.

It may be preferable to incorporate another closing element in the side access. The closing element can be a valve.

In case that any medicine is added via the side access it may be preferable that the valve can be synchronized with (or operated in view of) the closing elements provided for closing the bypass and the flow region. In particular, the closing element at the side access should close once the outlet opening is open, the closing element at the bypass is closed, and the closing element at the flow region is open. In that case expiratory gas flows along the second flow path. Any medicine added to the second flow path would not be transported to the patient but via the outlet opening to the outside.

The side access also provides for a possible connection for a side port capnometry line. Via this side port capnometry line a small sample of gas can be removed via the side access from the expiratory gas flowing along the second flow path for measuring the carbon dioxide concentration. The sample of gas is removed by a use of a suctioning compressor/pump so that the sample is directed into the capnograph.

The incorporation of a capnograph permits ongoing determination of the efficiency of the ventilation (ventilation decreasing or increasing over time).

Direct or indirect attachment of a volumetric gas flow meter or pressure meter via the side access is also conceivable.

In another special embodiment, a main stream capnograph (generally known in the art) can be positioned preferably between the connection of bypass and branching piece and the line connector.

A typical main stream capnograph comprises a small tube made of special material being positioned in the respiratory circuit (main stream), here in the second flow path, for example in the branching piece or in the lumen through which at least the second flow path is conducted. An infrared light is beamed through the small tube so that the diffraction of the gas flow inside the small tube is measured and calculated into a carbon dioxide concentration. The amount of light absorbed depends on the number of carbon dioxide molecules present in the gas flow.

Major advantage of a main stream capnograph is that the capnograph is not brought into direct contact with the expiratory gases, so that there is no risk of contamination and also no risk of damaging the system. A side port capnograph can be damaged by high gas pressures. This can occur incidentally, for example when there is an obstruction somewhere along the flow paths.

According to a preferred embodiment the suctioning compressor/pump of the side port capnometry line can be used for deflation of a cuff, which is provided to at least partially seal of the airway of a patient and which is positioned on the outside of a lumen. The lumen is being connected to the line connector and is being inserted into the airway of the patient. This arrangement can function as an emergency procedure so that in case of over pressurization of the airway the cuff can be deflated so that gas can bypass the lumen and the gas flow reversing element and exit to the outside. This emergency cuff-deflation procedure can in particular be incorporated as feature to the below mentioned methods of operation and ventilation.

In particular, the gas flow reversing element comprises several side accesses in the area of the branching piece.

It is also preferable for the pressure connector and/or the line connector, and if appropriate for the side access, to be designed as a Luer lock, in order to permit pressure-tight connections to standard components.

The gas flow reversing element according to the present invention allows choosing if the inspiratory gases are to be supplied to the patient's airways via the third flow path or via the fourth flow path. Further, the gases can be removed from the patient's airway via the second flow path, if a volumetric flow rate is provided along the first flow path.

The gas flow reversing element according to the present invention is especially designed to function in fully automated ventilation systems. In particular, the outlet opening can be connected to a ventilation system, so that the expiratory gases (as well as the inspiratory gases provided via the first flow path) are not being pushed into the open air. Further, these gases flowing via the outlet opening can be used in a closed loop ventilation system, so that a certain (constant) concentration of for example anesthesia damp can be maintained.

In particular, the gas flow reversing element can be connected to a fully automated ventilation system. In that case, the gas flow reversing element is operated at a distance to the patient. At a distance means in this case that the length of the lumen between the line connector (the connection of the lumen to the gas flow reversing element) and the point of entering into the patient is at least 40 cm [centimeter].

The gas flow reversing element can be designed as disposable part since its flow channels (all parts of the gas flow reversing element which are in direct contact with gas flowing through the gas flow reversing element) are in direct contact with the patient's expiratory gas flow. In that case it is preferable that as many parts as possible are not brought in direct contact with the patient's expiratory gas flow. For example, valves can be designed as scissor valves or pinch valves as explained above. Scissor valves or pinch valves pinch the flow channels from the outside. It is for that reason that at least parts of the flow channels of the gas flow reversing element are flexible so that they can be pinched by scissor or pinch valves.

In the following the term scissor valve encompasses both scissor valves and pinch valves.

Preferably, the valve for manipulating/closing/opening the inflow region, the flow region and/or the bypass is part of the (disposable) gas flow reversing element.

According to preferred embodiment an HME filter (Heat and Moisture Exchange filter) is positioned between the line connector and the patient. The HME filter blocks the passage of bacteria and viruses so that the gas flow reversing element can be used for a considerable number of patients without having to be disposed or cleaned.

It is further advantageously, if the gas flow reversing element is connected to a fully automated ventilation system in a position in which at least the connecting line and/or the bypass and/or the flow region are arranged in a vertical position in which any debris such as mucus, blood, other liquids and (tissue) particles will move from top to bottom (in direction of gravity). In that way, pollution of the automated ventilation systems by droplets or else, which stem from areas of flow channels of the gas flow reversing element through which expiratory gas from the patient is flowing, can be prevented.

According to a preferred embodiment, the connecting line and/or the bypass and/or the flow region each have an average (or maximum) inner diameter of at maximum 6 mm [millimeter], preferably at maximum 4 mm, and in particular at maximum 2.5.

The gas flow reversing element can also be operated in the direct vicinity of a patient. In direct vicinity means in this case that the length of the lumen between the line connector (the connection of the lumen to the gas flow reversing element) and the point of entering into the patient is at maximum 40 cm [centimeter].

According to another preferred embodiment, at least the valve for manipulating/closing/opening the inflow region, the flow region and/or the bypass is arranged outside of the gas flow reversing element.

Preferably, the gas flow reversing element comprises a bypass and a flow region which are connected to a bypass and a flow region provided outside of the gas flow reversing element (for example as part of a fully automated ventilation system).

The features described above in connection with the gas flow reversing element are not limited in their application. They can as well be combined with the method of operating the gas flow reversing element, with the method for ventilation of a patient or with the method for controlling expiration which are described in the following, and vice versa.

The invention is further related to a method for operating a gas flow reversing element according to the invention for selectively generating a gas flow from or to a line connector, in particular for connection of a lumen or a multitude of lumen that can be inserted into the airway of a patient, for gas exchange in sealed or partially sealed areas inside of the patient. The method can further be applied in cases of ventilation of only partial areas of the airway of a patient. A gas pressure, in particular inspiratory gas pressure, is applied to the pressure connector, and, in order to generate a high pressure gas flow to the line connector along the third flow path, the outlet opening and the flow region are closed. In order to generate a gas flow from the line connector in the direction of the outlet opening flowing along the second flow path, the outlet opening and the flow region are opened and the bypass is closed.

The invention is further related to a method for ventilating a patient, or assisting the breathing of a patient, using a gas flow reversing element according to the invention, in which method the line connector is attached to one of a lumen, a needle, a catheter or a multitude of lumen, which is inserted into the airway of a patient. The pressure connector is connected to a compressed gas source, in particular an inspiratory gas source, and an excess pressure of between 0.5 and 8 bar above atmospheric pressure is set up. With the outlet opening and the bypass closed the gas therefore passes into the patient's airway via the fourth flow path, wherein with the outlet opening opened and the bypass closed gas is conveyed out from the patient's airway via the line connector along the second flow path. With the flow region and the outlet opening closed and the bypass opened a high pressure gas flow is provided into the patient's airway via the bypass along the third flow path. This method of ventilation is in particular conducted during weaning procedure.

In particular, in the above mentioned methods the outlet opening is opened at intervals and for at least long enough to ensure that a characteristic measured value, in particular the carbon dioxide content, of the gas or gas mixture aspirated from the airway can be determined. In that respect the gas flow reversing element comprises a measuring device (preferably a side port or main stream capnograph) which is attached to a side access of the branching piece or to the branching piece directly as stated above.

In particular, the patient is ventilated only (and completely) via the gas flow reversing element. That means that all volumetric gas flows from or to the patient pass through the gas flow reversing element. In particular, the complete volumetric gas flow of inspiratory gas being provided to the patient's airways is provided via the fourth flow path and/or via the third flow path. Further, the complete volumetric gas flow of expiratory gas from the patient's airways is forwarded via the second flow path through the gas flow reversing element.

In certain applications it might be preferable to allow all of or at least parts of the expiratory gas to flow out of the patient's airways without further support of the gas flow reversing element. In that case expiratory gas may flow from the patient's airways directly to the outside without passing through the gas flow reversing element.

In particular, it is proposed that the lumen, which is inserted into the airway of the patient and is connected to the line connector, is provided with a cuff so that the airway of the patient around the lumen is at least partially obstructed by the inflated cuff. It is proposed that the ventilation of the patient is conducted via the gas flow reversing element, wherein the cuff is deflated at the time when gas is conveyed out from the patient's airway via the line connector along the second flow path, so that expiratory gas from the patient's airway is allowed also to bypass the lumen and the cuff and to exit to the outside by bypassing the gas flow reversing element. This method is advantageously applied during weaning of a patient. In that way the patient can gradually be accustomed again to autonomous breathing activity.

In particular, the lumen which is inserted into the airway of the patient and is connected to the line connector has a cross sectional area (through which the gas flow is directed) of at most 50 mm$^2$, preferably at most 15 mm$^2$, in particular at most 10 mm$^2$, or at most 7 mm$^2$.

In particular, the length of the lumen (distance between line connector at the gas flow reversing element and distal end of the lumen which is positioned inside the patient) is at least 60 cm, preferably at least 100 cm.

With the gas flow reversing element it is possible to fully ventilate a patient through a single lumen. It is especially advantageous, that the full ventilation can be conducted via a very small lumen (small cross sectional area). Further, by using small lumen (less than 50 mm$^2$ cross sectional area or less) the dead space (volume of lumen roughly between line connector and distal end of lumen which is positioned inside patient) inside the lumen is small. Since the dead space inside the lumen is small, high frequency (up to 100 breaths per minute or even more), low flow rate ventilation can be conducted as well (less than 2 l/min).

In particular, the use of the gas flow reversing element is advantageous because possible clogging of the flow paths through the gas flow reversing element and through lumen, which are connected to the gas flow reversing element, can effectively be prevented. This is because the gas flow is conducted in both directions through at least parts of the flow paths so that obstructions, stemming from blood, tissue ore else can be effectively removed.

Further, a method for controlling expiration is proposed in which the expiration phase of ventilation of a patient is being controlled. According to the method the expiratory volumetric gas flow is being regulated, wherein this regulation is conducted based on measurements of the pressure of the expiratory gas flow. The method comprises at least the following steps:
1. Measuring the pressure (static and/or dynamic) of the expiratory gas flow;
2. Regulating the expiratory volumetric gas flow; wherein step 2. is conducted based on the measured values of step 1.

In particular, the method for controlling expiration is conducted with a gas flow reversing element according to the invention and/or as part of the methods for operating the gas flow reversing element and ventilating a patient. Preferably, the method for controlling expiration can be conducted with any ventilation device that allows for controlling the expiratory volumetric gas flow from a patient. Preferably, the method refers to an expiratory phase, in which the expiratory gas flow is exclusively passing through a lumen and a ventilation device (such as the gas flow reversing element in conjunction with lumen and inflated cuff).

The method is applied in view of the problem that in the first phase of expiration usually a large expiratory volumetric gas flow occurs which decreases further until inspiration starts/is initiated again. This high value of expiratory volumetric gas flow at the beginning of the expiration phase can lead to expiratory shear stress of the lungs of the patient. It is especially in this phase of ventilation that the patient can be injured due to shear stress.

In particular, the method is directed to reduce the expiratory volumetric gas flow in this first phase of expiration. It proposed that for the specific regulation of the expiratory volumetric gas flow the pressure of the expiratory volumetric gas flow and/or the pressure inside the flow path for the expiratory volumetric gas flow is being measured (in case of the gas flow reversing element the volumetric gas flow along the second flow path or the second flow path). Based on the measured values of the pressure the expiratory volumetric gas flow is being regulated (in case of the gas flow reversing element via the closing elements and/or the pressure provided at the pressure connector).

In particular, the method is applied to ensure an even (uniform) reduction of the pressure of the expiratory volumetric gas flow and/or of the pressure inside the (ventilated part of the) lungs of the patient during the expiration phase of ventilation.

Preferably, steps 1. and 2. of the method are conducted repetitively (iteratively) so that constant monitoring of pressure and constant regulation of expiratory volumetric gas flow is possible.

Preferably the method for controlling expiration is conducted with a gas flow reversing element (with or without bypass) in conjunction with a lumen and a cuff. The gas flow reversing element allows for complete ventilation of a patient via a single lumen (expiration and inspiration), wherein the airway is sealed off to the outside by a cuff. Preferably, this lumen, being connected to the line connector and being inserted into the patient's airways, has a small inner diameter, for example 6 mm or less, preferably 4 mm or less, in particular 2.5 mm or less, and/or a cross sectional area of at most 50 mm$^2$, preferably at most 15 mm$^2$, in particular at most 10 mm$^2$ or at most 7 mm$^2$. In that case the flow resistance along the expiratory gas flow path (second flow path) is large so that the expiratory volumetric gas flow even in the first phase of expiration is limited sufficiently. In fact, in case of such high flow resistance the expiratory volumetric gas flow along the second flow path has to be supported by a gas flow along the first flow path. In that way shear stresses can be prevented.

Illustrative embodiments of the invention, which do not however limit the invention, are explained in more detail below with reference to the schematic drawings, in which.

Identical reference numerals in the figures refer to the same devices.

Figure 1:
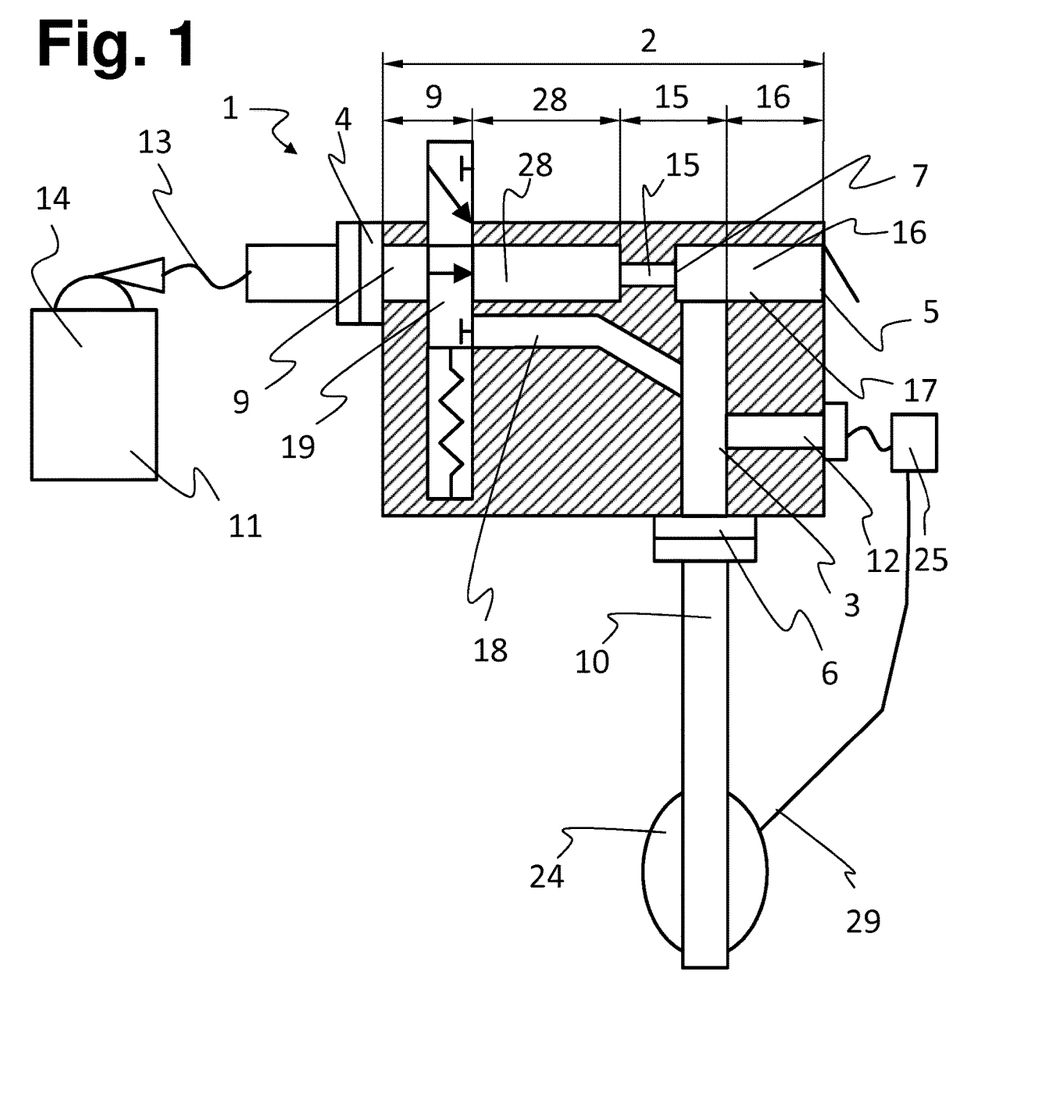
FIG. 1: shows a longitudinal section through a gas flow reversing element, with peripheral devices indicated.

FIG. 1 shows a longitudinal section through a gas flow reversing element 1 with a main piece 2 which connects a pressure connector 4 to an outlet opening 5. The pressure connector 4 can be connected by a connecting line 13 to a gas supply 14 which is under excess pressure in a compressed gas source 11. A compressed oxygen cylinder is generally made available for the emergency care of patients. Furthermore, complex gas mixtures can be provided as gas supply 14. Extending off from the main piece 2 is a branching piece 3, which leads to a line connector 6. In the main piece 2, an inflow region 9, a flow region 28, a nozzle region 15 with a nozzle 7, and a mixing region 16 with a mixing channel 17 are realized. Inside the nozzle region 15 there is a nozzle 7 through which gas can flow from the pressure connector 4 to the outlet opening 5. This nozzle 7 lies near the branching piece 3, such that the gas flowing through the nozzle 7 to the outlet opening 5 generates an underpressure in the branching piece 3. Here, the principle of a gas jet pump is used. However, it is possible to choose any arrangement that is able to generate a suction effect by means of a gas flow. At least the outlet opening 5 should be able to be closed, for example with a scissor-valve or pinch valve as closing element 19.

The gas flow reversing element 1 further comprises a bypass 18 connecting the pressure connector 4 and the line connector 6. A gas can therefore flow via the inflow region 9, the bypass 18 and the branching piece 3. At least the bypass 18 and the flow region 28 are closable by at least one closing element 19, so that the gas can bypass the nozzle 7 in the nozzle region 15 via the bypass 18. Here, the at least one closing element 19 is a 3/2-way valve. In the position shown (here referred to as first position) the 3/2-way valve connects the pressure connector 4 and the inflow region 9 with the flow region 28 and the nozzle region 15. The connection to the bypass 18 is closed.

The branching piece 3 also has a closable side access 12 through which medicine can be added or probes be inserted. Furthermore, a measuring device 25 can be connected with the side access 12 so that certain parameters can be monitored, for example the content of carbon dioxide in expiratory gas.

Further, the pressure present in the branching piece 3 can be measured with a pressure measuring device 25 via the side access 12.

Further, the side access 12 can provide as connection for a side port capnometry line. Via this side port capnometry line a small sample of gas can be removed via the side access 12 from the expiratory gas flowing along the second flow path 21 (refer to FIG. 2) for measuring the carbon dioxide concentration. The sample of gas is removed by a use of a suctioning compressor/pump so that the sample is directed into the capnograph (here shown as measuring device 25).

According to a preferred embodiment the suctioning compressor/pump (here shown as measuring device 25) of the side port capnometry line can be used for deflation of a cuff 24, which is provided to at least partially seal of the airway of a patient and which is positioned on the outside of the lumen 10. The lumen 10 is being connected to the line connector 6 and is being inserted into the airway of the patient. The compressor pump can be connected to the cuff 24 via a separate supply line 29. The supply line 29 can also be arranged inside the gas flow reversing element 1 so that the supply line 29 can also be integrated into the lumen 10, for example into the sidewall of the lumen 10. This arrangement can function as an emergency procedure so that in case of over pressurization of the airway the cuff 24 can be deflated so that gas from the airway of the patient can bypass the lumen 10 and the gas flow reversing element 1.

Each of the connectors 4, 6 is preferably designed as a Luer lock.

Figure 2:
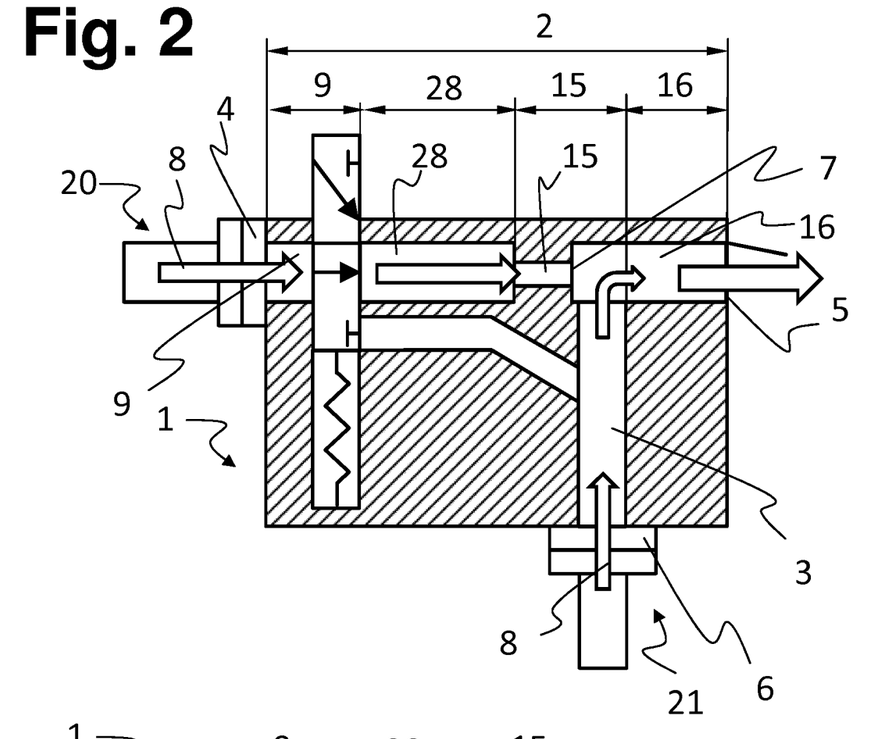
FIG. 2: shows the gas flow reversing element in use with gas flowing along the first and second flow paths.

FIG. 2 shows the gas flow reversing element 1 in use with main piece 2 and branching piece 3. The 3/2-way valve as closing element 19 is in the first position. Thus the inspiratory gas provided by the compressed gas source 11 (not shown) to the gas flow reversing element 1 via the pressure connector 4 flows along the first flow path 20 subsequently through the inflow region 9, the flow region 28, the nozzle region 15 and through the nozzle 7 into the mixing region 16 to the outlet opening 5, with the outlet opening 5 opened. Passing through the nozzle 7 the gas flow 8 flowing along the first flow path 20 generates an underpressure in the nozzle region 15 so that another gas flow 8 is generated in the branching piece 3 flowing along a second flow path 21 from the line connector 6 and subsequently through the branching piece 3, through the nozzle region 15 and through the mixing region 16 to the outlet opening 5.

Figure 3:
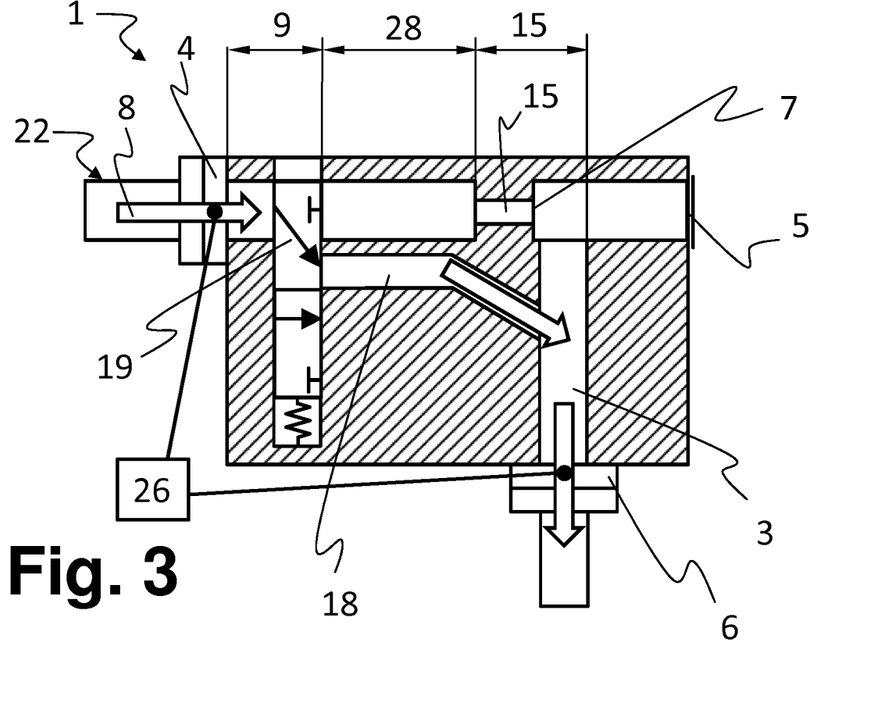
FIG. 3: shows the gas flow reversing element in use with gas flowing along the third flow path.

FIG. 3 shows the gas flow reversing element 1 in use with main piece 2 and branching piece 3, wherein the 3/2-way valve as closing element 19 is in the second position. In this position the 3/2-way valve connects the pressure connector 4 with the bypass 18. The connection between pressure connector 4 and nozzle region 15 via flow region 28 is disconnected. Thus the inspiratory gas provided by the compressed gas source 11 (not shown) to the gas flow reversing element 1 via the pressure connector 4 flows along the third flow path 22 subsequently through the inflow region 9, through the bypass 18 into the branching piece 3 and to the line connector 6, with the outlet opening 5 being closed. For the third flow path 22, connecting the pressure connector 4 and the line connector 6 via the bypass 18, the gas flow 8 experiences a first pressure loss deltaP1 26 at certain flow rates.

This first pressure loss deltaP1 26 along the third flow path 22 is much smaller than the second pressure loss delta P2 27 along the fourth flow path 23 for identical volumetric flow rates. Therefore, for a certain pressure provided at the pressure connector 4 by the compressed gas source 11 (not shown) a larger volumetric gas flow rate is achieved along the third flow path 22 than it would be possible along the fourth flow path 23.

Figure 4:
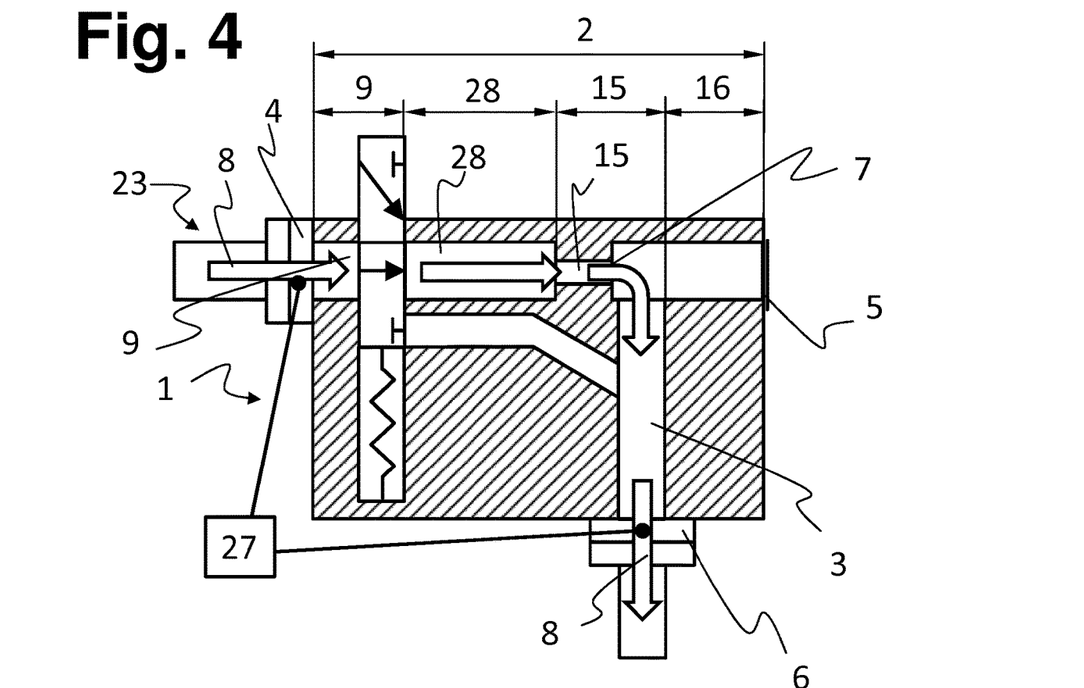
FIG. 4: shows the gas flow reversing element in use with gas flowing along the fourth flow paths.

FIG. 4 shows the gas flow reversing element 1 in use with the 3/2-way valve as closing element 19 in the first position. Thus the inspiratory gas provided by the compressed gas source 11 (not shown) to the gas flow reversing element 1 via the pressure connector 4 flows along the fourth flow path 23 subsequently through the inflow region 9, through the nozzle region 15 and through the nozzle 7 into the branching piece 3 and to the line connector 6, with the outlet opening 5 being closed. For the fourth flow path 23, connecting the pressure connector 4 and the line connector 6 via the inflow region 9, the flow region 28, the nozzle region 15, and the branching piece 3, the gas flow experiences a second pressure loss deltaP2 27.

Figure 5:
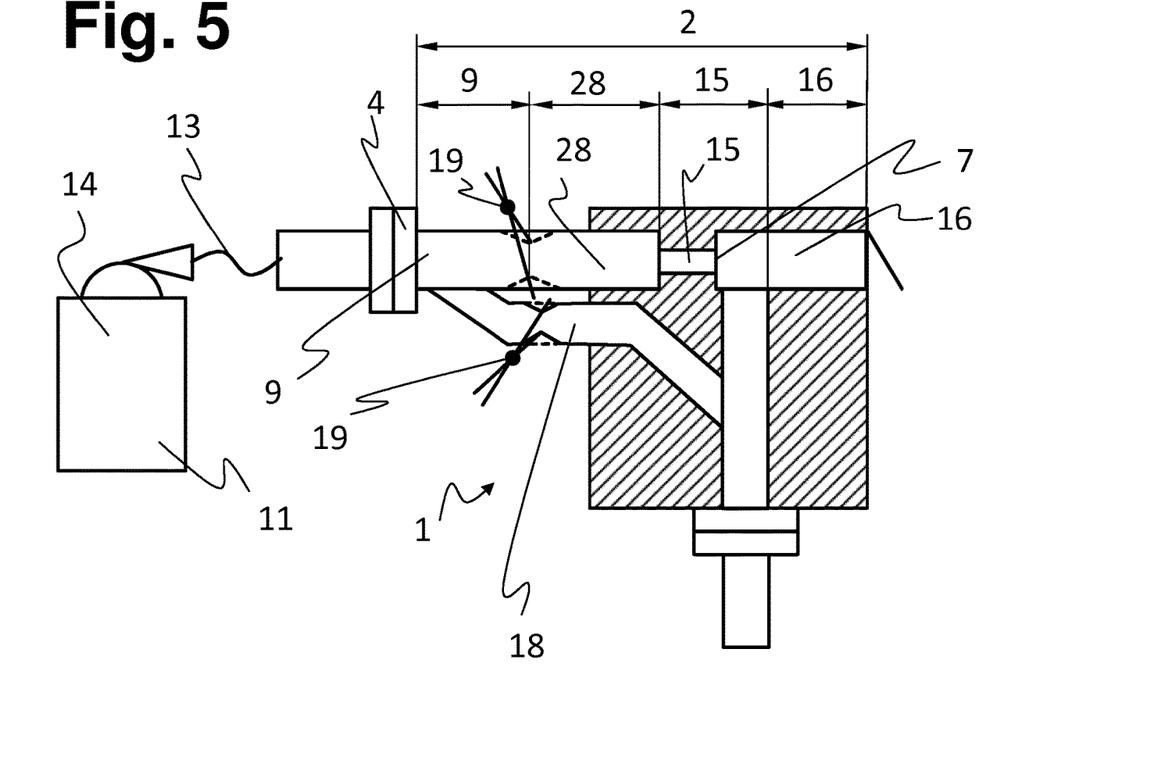
FIG. 5: shows the gas flow reversing element with scissor vales as closing elements.

FIG. 5 shows the gas flow reversing element 1 with scissor valves as closing elements 19. In this case, scissor valves are positioned outside of the gas flow reversing element 1. At least parts of inflow region 9, flow region 28 and bypass 18 are also positioned outside of gas flow reversing element 1. Inflow region 9, flow region 28 and bypass 18 outside of the gas flow reversing element 1 are connected to inflow region 9, flow region 28 and bypass 16 of the gas flow reversing element.

All closing elements 19 disclosed (scissor valves, 3/2-way valve) can be pneumatically or electronically or manually controlled. In particular, all closing elements 19 are designed to gradually reduce and/or increase the volumetric flow rate along the flow path through the valve.

Figure 6:
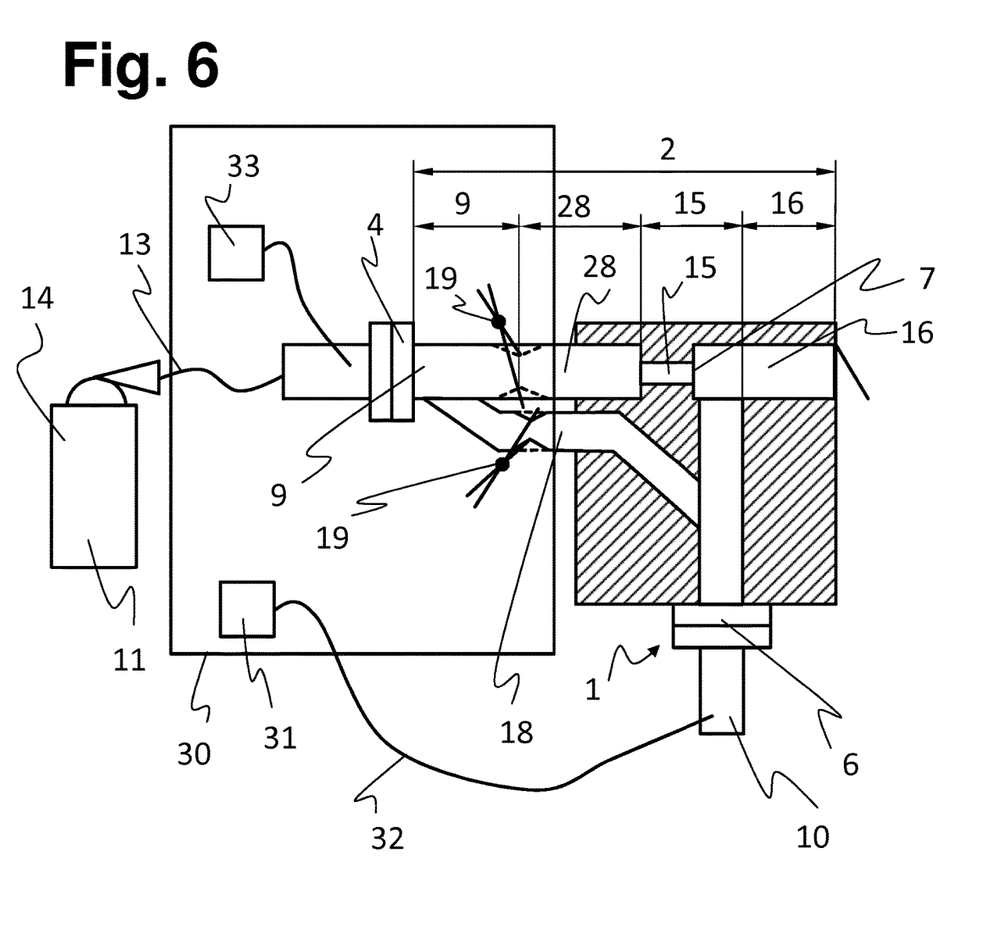
FIG. 6: shows the gas flow reversing element of FIG. 5 and a control unit.

FIG. 6 shows the gas flow reversing element 1 of FIG. 5 and a control unit 30. The control unit 30 is for example a fully automated ventilation system to which the gas flow reversing element 1 is connected. In this preferred embodiment scissor valves 19 are integrated into the control unit 30. The gas flow reversing element 1 is connected to the control unit 30 by flow region 30 and bypass 18.

It is emphasized that gas flow reversing elements 1 of FIGS. 1 to 4 can as well be connected to a control unit 30.

In any case it is important to measure the pressure inside the lungs of the patient. This is preferably done in two separate ways, for safety reasons (in case one of them fails). Preferably, the lumen 10 (or one of the lumen) connected to the line connector 6 will be connected to a first pressure sensor 31 in a control unit 30 that will measure the lung pressure continuously during ventilation. The connection between pressure sensor 31 and control unit 30 is realized via an extension line 32, which could be a separate line or integrated into the lumen 10 used for ventilation. This is the main pressure measurement, providing medical staff with the data needed.

Further, there is preferably a separate second pressure sensor 33 in the control unit 30, wherein this second pressure sensor is connected to the inflow region 9 or to the pressure connector 4. This second pressure sensor 33 only measures the pressure when the ventilation is paused. This is because it is fairly impossible to provide for a reliable value of lung pressure through the ventilation lumen (lumen 10, line connector 6, bypass 18 or nozzle region 15 and flow region 28, inflow region 9) when high inspiratory or expiratory flows are running through. In normal mode, this is just a safety feature and it is a check to see if the main pressure measurement (via the first pressure sensor 31) is still working well (first pressure sensor 31 could be broken, but also the lumen 10 connected to the line connector 6 could be obstructed etc.). Therefore, after n numbers of inspiration (n=1 to n=10) and n numbers of expiration, the ventilation is paused for a very short moment (~50 to 100 ms [milliseconds]), the gas flow is stopped and a viable pressure measurement can be performed via the ventilation lumen by the second pressure sensor 33.

Obviously, the gas flow reversing element 1 can be operated with only the first pressure sensor 31 or second pressure sensor 32.

LIST OF REFERENCE NUMERALS

1 Gas flow reversing element
2 Main piece
3 Branching piece
4 Pressure connector
5 Outlet opening
6 Line connector
7 Nozzle (injector nozzle)
8 Gas flow
9 Inflow region
10 Lumen
11 Compressed gas source
12 Side access
13 Connecting line
14 Gas supply
15 Nozzle region
16 Mixing region
17 Mixing channel
18 Bypass
19 Closing element
20 First flow path
21 Second flow path
22 Third flow path
23 Fourth flow path
24 Cuff
25 Measuring device
26 first pressure loss deltaP1
27 second pressure loss deltaP2
28 flow region
29 supply line
30 control unit
31 first pressure sensor
32 extension line
33 second pressure sensor

The invention claimed is:

1. A gas flow reversing element for the use of a gas supply under excess pressure for selectively generating a gas flow from or to a line connector which can be connected to or inserted into an airway of a patient, said gas flow reversing element being designed as a main piece, the main piece at least comprising an inflow region, a flow region, a nozzle region and a mixing region, and further a branching piece, the inflow region connecting a pressure connector, for connection to the gas supply, to at least one closable outlet opening arranged in the mixing region, and the branching piece connecting the nozzle region of the main piece to the line connector, wherein a nozzle is configured and arranged in the nozzle region in such a way that, a gas flow flowing along a first flow path through the main piece from the pressure connector subsequently through the inflow region, the flow region, the nozzle region and through the nozzle into the mixing region to the outlet opening, with the outlet opening opened, can generate a gas flow in the branching piece flowing along a second flow path from the line connector and subsequently through the branching piece, through the nozzle region and through the mixing region to the outlet opening, wherein further a gas flow entering the gas flow reversing element via the pressure connector can flow along a fourth flow path subsequently through the inflow region, through the nozzle region and through the nozzle into the branching piece, and to the line connector, with the outlet opening being closed, and wherein the gas flow reversing element further comprises a bypass connecting the pressure connector and the line connector so that a gas flow can bypass the nozzle in the nozzle region, and flow along a third flow path to the line connector that can be connected to or inserted into the airway of the patient via the inflow region, the bypass, and the branching piece when the connection between the pressure connector and the nozzle region via the flow region is disconnected, and wherein at least the bypass and the flow region are closable by at least one closing element, so that the gas flow can bypass the nozzle in the nozzle region via the bypass along the third flow path when the at least one closing element is in position to connect the pressure connector with the bypass.

2. The gas flow reversing element according to claim 1, wherein the at least one closing element is a 3/2-way valve.

3. The gas flow reversing element according to claim 1, wherein two scissor valves are provided as the at least one closing element, one scissor-valve being positioned in the third flow path, the other scissor-valve being positioned in the first flow path.

4. The gas flow reversing element according to claim 1, wherein, for an excess pressure of 1 to 8 bar above atmospheric pressure at the pressure connector and with the outlet opening being closed, the third flow path, connecting the pressure connector and the line connector via the bypass, has a first pressure loss deltaP1; and the fourth flow path, connecting the pressure connector and the line connector via the inflow region, the flow region, the nozzle region, and the branching piece, has a second pressure loss deltaP2, wherein deltaP2>2*deltaP1.

5. The gas flow reversing element according to claim 1, wherein the mixing channel and the nozzle are configured and arranged in the main piece in such a way, by a gas flow flowing along the first flow path with the outlet opening opened, the gas flow flowing along the second flow path can also be generated, specifically with a volumetric flow rate which, at an excess pressure of 0.5 to 8 bar above atmospheric pressure at the pressure connector, is at least 1 liters per minute.

6. The gas flow reversing element according to claim 1, wherein the gas supply under excess pressure comprises inspiratory gases.

7. The gas flow reversing element according to claim 1, wherein the nozzle comprises an injector nozzle.

8. The gas flow reversing element according to claim 1, wherein when the closing element is in a first position, the closing element connects the pressure connector and the inflow region with the flow region and the nozzle region, wherein the closing element in the first position further causes the connection to the bypass to be closed;

and wherein when the closing element is in the second position the closing element connects the pressure connector with the bypass and causes the connection between the pressure connector and the nozzle region, via the flow region, to be disconnected.

9. The gas flow reversing element according to claim 1, wherein the gas flow entering the gas flow reversing element flows into the line connector via one of two separate paths defined in the gas flow reversing element, the two separate paths including: i) the third flow path defined by the bypass connecting the pressure connector and the line connector so that the gas flow bypasses the nozzle in the nozzle region, with the gas flow flowing along the third flow path to the line connector via the inflow region, the bypass, and the branching piece when the connection between the pressure connector and the nozzle region via the flow region is disconnected, and ii) the fourth flow path in which the gas flow flows through the inflow region, the nozzle region, the nozzle, into the branching piece, and to the line connector, with the outlet opening being closed.

* * * * *